(12) United States Patent
Sherman et al.

(10) Patent No.: US 9,695,392 B2
(45) Date of Patent: Jul. 4, 2017

(54) APPARATUS FOR MIXING AND DISRUPTION OF CELL AND TISSUE SAMPLES IN VESSELS

(71) Applicants: Yury Sherman, Roslindale, MA (US); Michael Sherman, Newton, MA (US); Ilya Alexandrov, Natick, MA (US)

(72) Inventors: Yury Sherman, Roslindale, MA (US); Michael Sherman, Newton, MA (US); Ilya Alexandrov, Natick, MA (US)

(*) Notice: Subject to any disclaimer, the term of this patent is extended or adjusted under 35 U.S.C. 154(b) by 0 days.

(21) Appl. No.: 14/958,747

(22) Filed: Dec. 3, 2015

(65) Prior Publication Data
US 2017/0159000 A1    Jun. 8, 2017

(51) Int. Cl.
*B01F 11/00* (2006.01)
*C12M 3/06* (2006.01)

(52) U.S. Cl.
CPC ......... *C12M 27/16* (2013.01); *B01F 11/0005* (2013.01); *B01F 11/0008* (2013.01); *C12M 27/14* (2013.01)

(58) Field of Classification Search
CPC . B01F 11/0005; B01F 11/0008; C12M 27/14; C12M 27/16
USPC .................................................. 366/213–214
See application file for complete search history.

(56) References Cited

U.S. PATENT DOCUMENTS

| | | | |
|---|---|---|---|
| 3,061,280 A * | 10/1962 | Kraft | B01F 11/0014 366/110 |
| 3,159,384 A * | 12/1964 | Davis | B01F 11/0014 211/74 |
| 3,819,158 A | 6/1974 | Sharpe | |
| 4,118,801 A | 10/1978 | Kraft | |
| 4,125,335 A | 11/1978 | Blume | |
| 4,202,634 A | 5/1980 | Kraft | |
| 4,295,613 A | 10/1981 | Moore | |
| 4,305,668 A | 12/1981 | Bilbrey | |
| 4,555,183 A | 11/1985 | Thomas | |
| 4,747,693 A | 5/1988 | Kahl | |
| 4,883,644 A * | 11/1989 | Perlman | B01L 9/06 366/110 |
| 5,195,825 A * | 3/1993 | Ringrose | B01F 11/0005 366/110 |
| 5,707,861 A * | 1/1998 | Sherman | C12M 23/48 211/78 |
| 5,769,538 A * | 6/1998 | Sherman | B01F 11/0008 366/198 |
| 7,204,637 B2 * | 4/2007 | Sherman | B01F 9/0021 366/214 |

* cited by examiner

*Primary Examiner* — Charles Cooley
(74) *Attorney, Agent, or Firm* — Bold IP, PLLC; Daniel Cole; Maki Imakura

(57) ABSTRACT

An apparatus for substantially horizontally oscillating one or more vessels containing a liquid, a solid, or a mixture thereof that operates to thoroughly disrupt and mix solid and liquid substances in vessels, like test tubes. The apparatus provides superior mixing through oscillation of the vessels both horizontal and vertical directions through the use of one or more springs and rotating mechanical components. The apparatus includes a circular rotating ring having a toothed circumference that rotates horizontally, at least one vessel support having a compartment configured to hold the one or more vessel vessels and a spring attached to the housing and in constant contact with each of the one or more vessel supports.

19 Claims, 13 Drawing Sheets

APPARATUS FOR MIXING AND DISRUPTION OF CELL AND TISSUE SAMPLES IN VESSELS

BACKGROUND

The present invention describes an apparatus and method for mixing and disintegrating materials in test tubes, particularly for those materials that may be difficult to disintegrate, such as tissues. Devices for these purposes are described in U.S. Pat. Nos. 3,819,158; 4,202,634; 4,295,613; 4,883,644; 4,118,801; 4,125,335; 4,305,668; 4,555,183; 4,747,693, 5,708,861, and 5,769,538.

The most common test tube disrupters use tube vibration technology. Tube vibration technology involves a vibrating surface against which test tubes are held by the operator. Vibration of the surface induces vibration of the contents of the tubes. Tube vibration disrupters are simple devices that have several drawbacks. They provide low power and are only effective for disruption of cells and tissues of low hardness. Additionally, they require that the operator have their hand in physical contact with the test tubes, thus subjecting them to the same physical vibrations, which may cause discomfort and increases the potential for receiving injury.

U.S. Pat. No. 5,769,538 discloses a more advanced tube striking technology to produce vibrations. A popular brand of disruptor or BULLET BLENDER® uses tube striking technology. The advantages of tube striking technology over tube vibration are that multiple tubes may be processed at once, and the operator need not remain in physical contact with the tubes during disruption. However, these striking-style disrupters have several drawbacks.

The transfer of the energy of the strike to the contents of the tube may be inefficient, being dissipated by the liquid media within the tube. This causes an increase in power usage and a decrease in effectiveness. This drawback is particularly disadvantageous when using larger test tubes or when disrupting harder tissues.

Strong periodic strikes cause significant vibration, which necessitates the use of vibration dampeners. This is particularly important for hard tissues, such as heart or kidney, which require strong strikes to adequately disrupt. These dampeners increase the weight and cost of the disrupters and increase the rigidity of connections between the parts. These strong strikes also increase the chance of destroying the test tube.

Tube strikers are extremely loud, and require expensive, large housings with inner sound isolation to dampen noise.

All of the above drawbacks limit the number of potential applications and increase the structural complexity of the devices and increase their weight, size, and production cost, and are particularly disadvantageous for disruption of larger test tubes and harder tissues.

SUMMARY

The present invention overcomes many of these drawbacks, and allows the user to disrupt small or large sample sizes and to process many samples simultaneously without cross-contamination. The invention provides enhanced disruption and mixing of cells and tissues in test tubes, in the presence of liquid substance and beads, by using a spring mechanism. The core innovation is the interacting of spring mechanisms and specific test tube supports to provide horizontal, vertical, or both horizontal and vertical oscillations of the test tubes. The invention combines the two major functions of oscillations and striking.

The tube support includes a body having a compartment that can accommodate a test tube. The spring mechanism attached to the test tube holder pushes the test tube holder horizontally, vertically, or both, depending on which type of oscillation (horizontal or vertical) is intended.

For horizontal oscillation, the mechanism includes a rotating ring having a number of curved steps along its inner edge, and springs which hold the test tube supports in constant contact with the inner stepped edge of the rotating ring. The curved steps of the rotating ring may be smooth (like a sine wave) or may have sharp edges. Due to the shape of the rotating ring edge, the test tube support receives horizontal oscillation, which is transferred to the contents of the test tube, which in turn generates chaotic movement and clashing of the beads with the cells and tissues. The more frequent and strong the clashes, the more effective the disruption process. In another embodiment, the curved steps are located on the outer edge of the rotating ring and test tubes supports are located around its periphery.

For vertical oscillation, the mechanism includes a rotating disk which has wedges, and springs which hold the test tube supports in contact with the rotating disk. The wedges on the disk are created in similar arrangement to those of the rotating ring, and may also be smooth or sharp-edged, and which are arranged on the disk in a circular pattern about the axis. Due to the shape of the rotating disk, the test tubes receive vertical oscillations, which are transferred to the contents of the test tube, which in turn generates chaotic movement and clashing of the beads with the cells and tissues. The more frequent and strong the clashes, the more effective the disruption process.

Horizontal and vertical mechanisms as described above may be used individual within a device, or in a device that includes both mechanisms. Some embodiments may include removable or replaceable rotating disks or rings, allowing the user to configure the type of oscillation to their intended purpose.

Embodiments of the invention permit use of a variety of test tube sizes and dimensions.

DEFINITIONS

Rotating Ring: A ring with either a curved or jagged inner or outer edge that is rotated laterally on a central axis.

Rotating Disk: A disk on which vertical wedges are configured in a circular shape around the axis.

DETAILED DESCRIPTION

FIGS. 1-12 show embodiments of a spring mechanism used for disruption of cells and tissues in test tubes.

Figure 1:
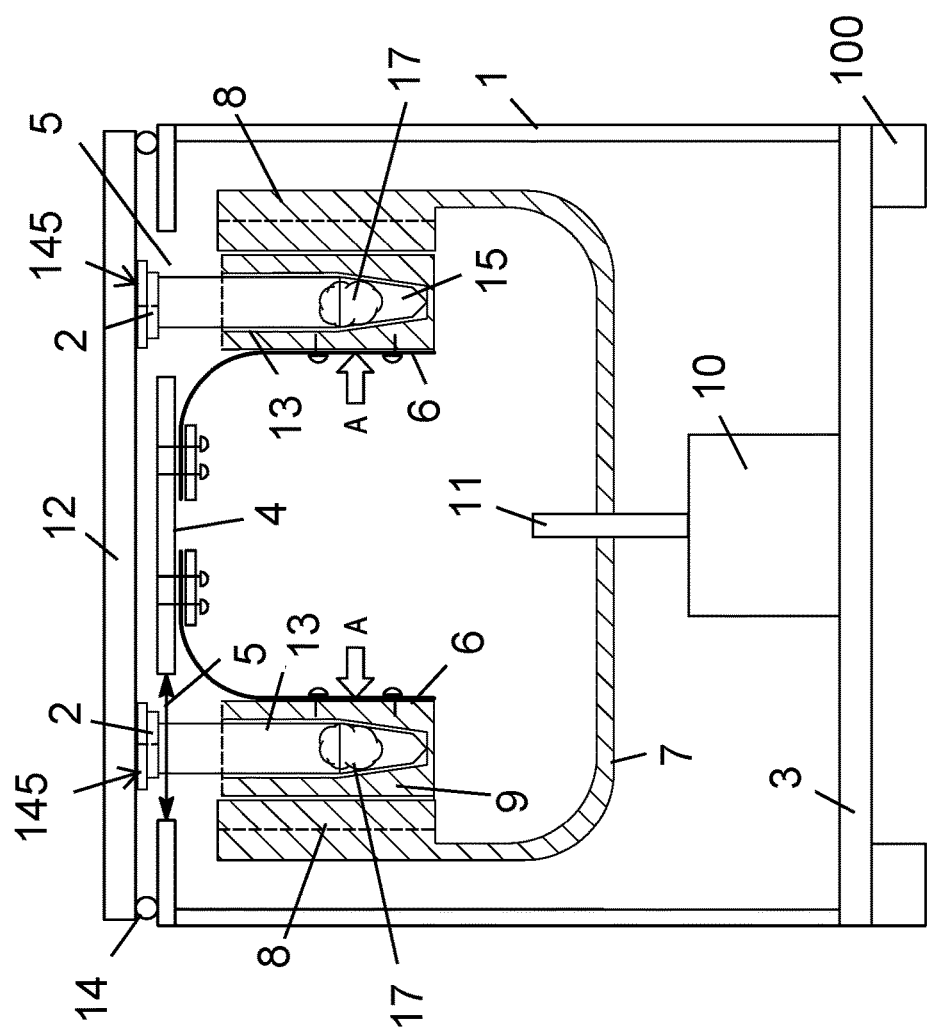
FIG. 1 shows a vertical cross-sectional view of an embodiment for horizontal oscillation intended for standard small volume 1.5-2.0 ml test tubes.

FIG. 1 is a side view of an embodiment wherein standard small test tubes 2 are placed in test tube supports 9 which are attached to centrally-mounted stationary springs 6. The springs 6 keep the test tube supports in constant contact with the inner edge of the rotating ring 8. Cell or tissue samples 17 along with beads are placed with a liquid buffer 15 in the tubes 2. The tubes 2 are displaced with respect to the central axis as the rotating ring rotates 8, causing the liquid buffer 15 clash with the beads. When the liquid buffer 15 and the beads clash, the tissue breaks up and disperses within the test tubes 2. The stronger and more frequent the clashes, the more effective the disruption and dispersion.

The device comprises a housing 1 with a top plate 4 and a base 3. An electric motor 10 drives a shaft 11 which rotates a bowl 7. A rotating ring 8 is integral to the inner side of the upper edges of the bowl 7. Tube supports 9 and compartments 13 are positioned radially about the motor shaft 11, inside and in constant contact with the rotating ring 8 as it rotates. There is also no gap between the tube support 13 and test tube 2.

In the embodiment shown in FIG. 1, flat L-shaped springs 6 are attached with screws to a top plate 4. The L-shaped springs 6 are also attached with screws to the tube supports 9. The springs 6 keep the tube supports 9 and tubes 2 in their suspended position, pressed against the rotating ring's inner edge.

Test tubes 2 may be loaded into their tube supports 9 manually. Therefore, the top plate 4 includes holes 5 whose diameter is larger than the diameter of the tube caps 145. Tubes 2 are inserted into their supports 9 though the holes 5.

The housing 1 has a removable cover 12 which is closed during operation. The main function of the closure is to prevent the tubes 2 from being ejected from their supports 9 while the supports are moving due to contact with the rotating ring 8. The gap between the tube caps 145 and the closure 12 should be minimal; in some embodiments a spring exerts vertical pressure on the tube cap to keep the tube in place. A sound damping gasket 14 is placed between the closure 12 and the top plate 4 along the outer perimeter. The gasket may be loose and secured by pressure or adhered to either the closure 12 or the top plate 4.

Figure 2:
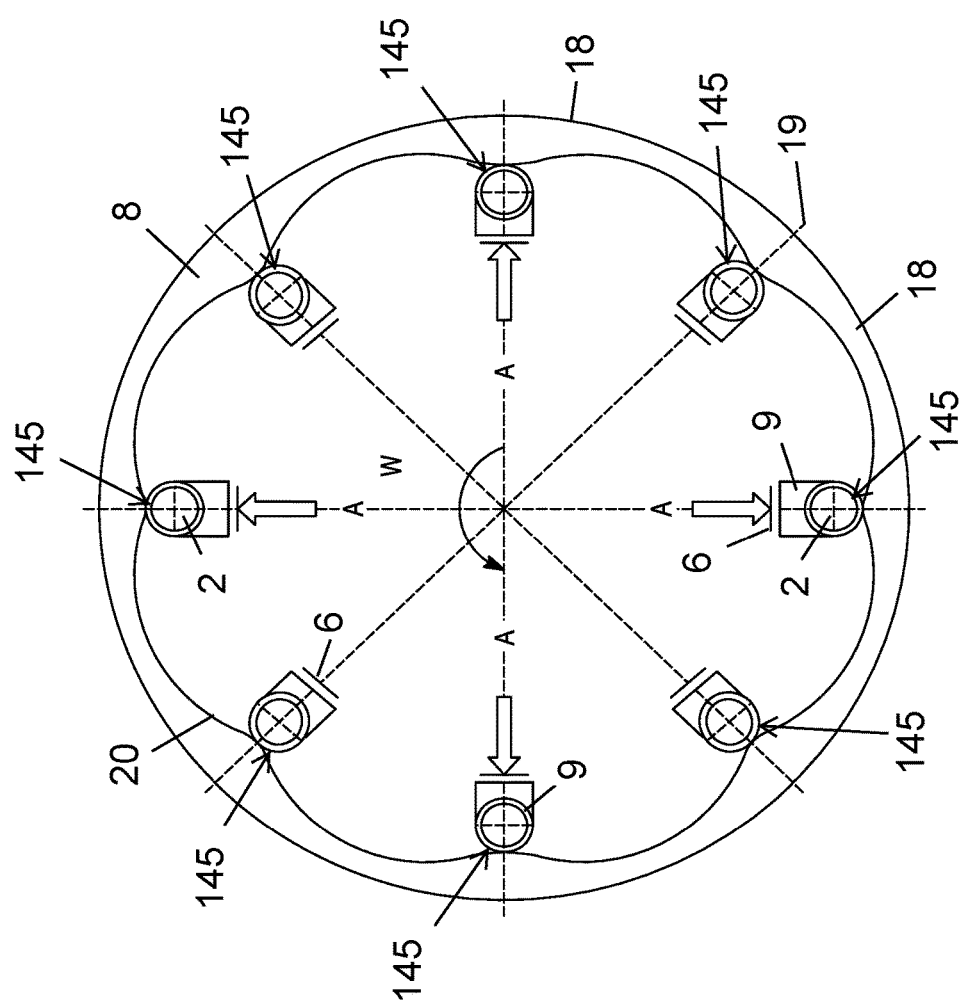
FIG. 2 shows a top section view of an embodiment for horizontal oscillation with a smooth, wave-like rotating ring and one small volume test tube in each of eight tube supports.

Also shown on FIG. 1 are feet 100 which support the entire structure. The feet are made of metal but could be made of rubber, or plastic or any material common in the art. The drum 7 and rotating ring 8 are rotated radially by axle 11 which is rotated by an electrical motor 10. As shown in FIG. 2, when rotating ring 8 is rotated counter-clockwise, each tube support 9, and its respective tube and contents, move laterally. Each support 9 is pressed against the ring's teeth 20. The ring's toothed surface 20 travels along the outer edge of the supports 9. This radial displacement and force inwardly on the tube supports 9 moves the tube's 2 beads and liquid buffer 15, which clash with one another inside the tubes 2.

For example, with eight tubes 2 agitated by eight teeth in the ring 8, rotating at 600 rpm, the tubes will be oscillated 80 times per second. Vibrations cause the beads to clash with each other and with the cells and tissues in between. These clashes cause disruption of the cells and tissues inside of the test tubes 2. Varying the speed of rotation of rotating ring 8, the size of teeth, and the distance between teeth, will cause corresponding changes to the amount and magnitude of the oscillation.

Figure 3:
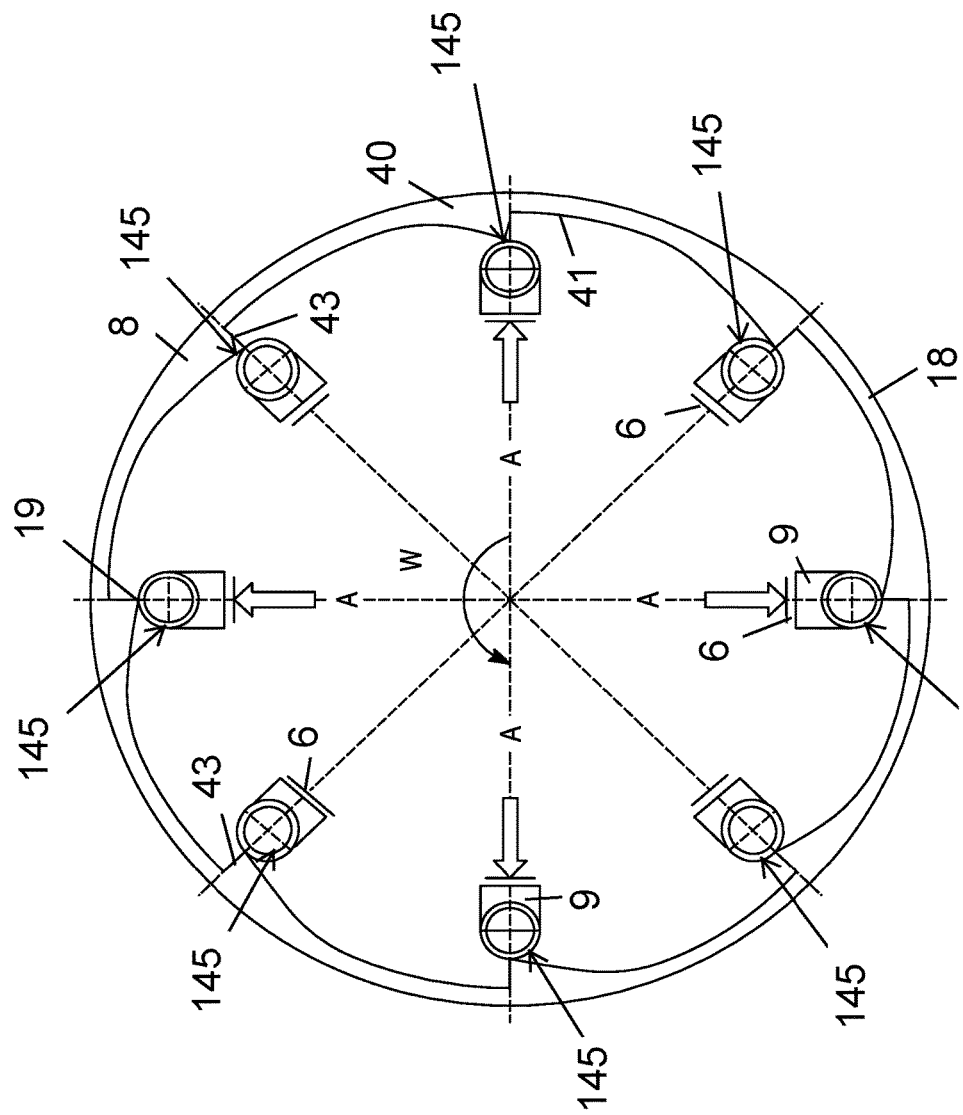
FIG. 3 shows a top section view of an embodiment for horizontal oscillation with a jagged, rotating ring and one small test tube in each of eight supports.

For some types of tissues, the disruption process must be accelerated to prevent long-term overheating. This acceleration is accomplished by sharpening the shape of the ring's teeth 40 (FIG. 3). The angular velocity is labeled as "w" in FIG. 3. In this embodiment, each tooth's recess point 18 and end protrusion point 19 is connected along the shortest radial line 43, forming a step between adjacent teeth. Due to this drastic step, the tube contents (liquid, cells/tissues and beads) jump or move suddenly with increased acceleration. These jumps release additional energy applied to beads, which intensify and increase their number of clashes within the test tube 2 with each other and the test tube contents.

To reduce noise of clashes between tube supports 9 and rotating ring teeth 8, a rubberized or otherwise sound-dampening layer can be applied to the ring 8 or to the tube supports 9.

Figure 4:
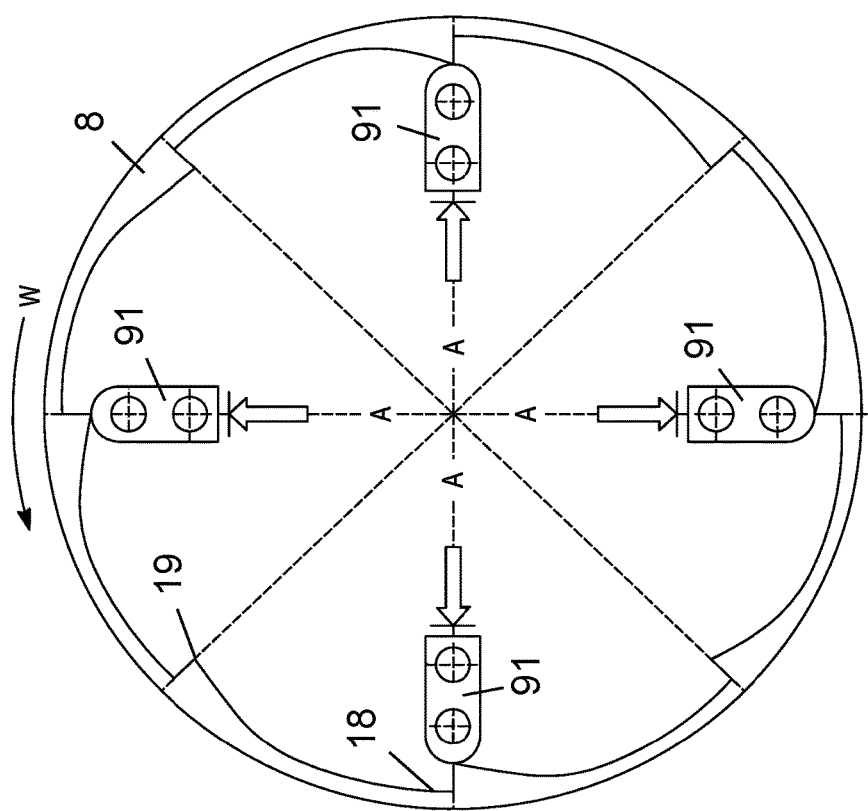
FIG. 4 shows a top section view of an embodiment with a jagged rotating ring and four tube supports, each supporting two test tubes.

Another embodiment shown in FIG. 4 shows a doubled tube capacity, holding eight tubes, radially paired. This embodiment has tube supports 91 which each house two tubes. This embodiment works in substantially the same way as the previously described embodiment, and it is more compact and efficient than other disrupters in the industry.

Figure 5:
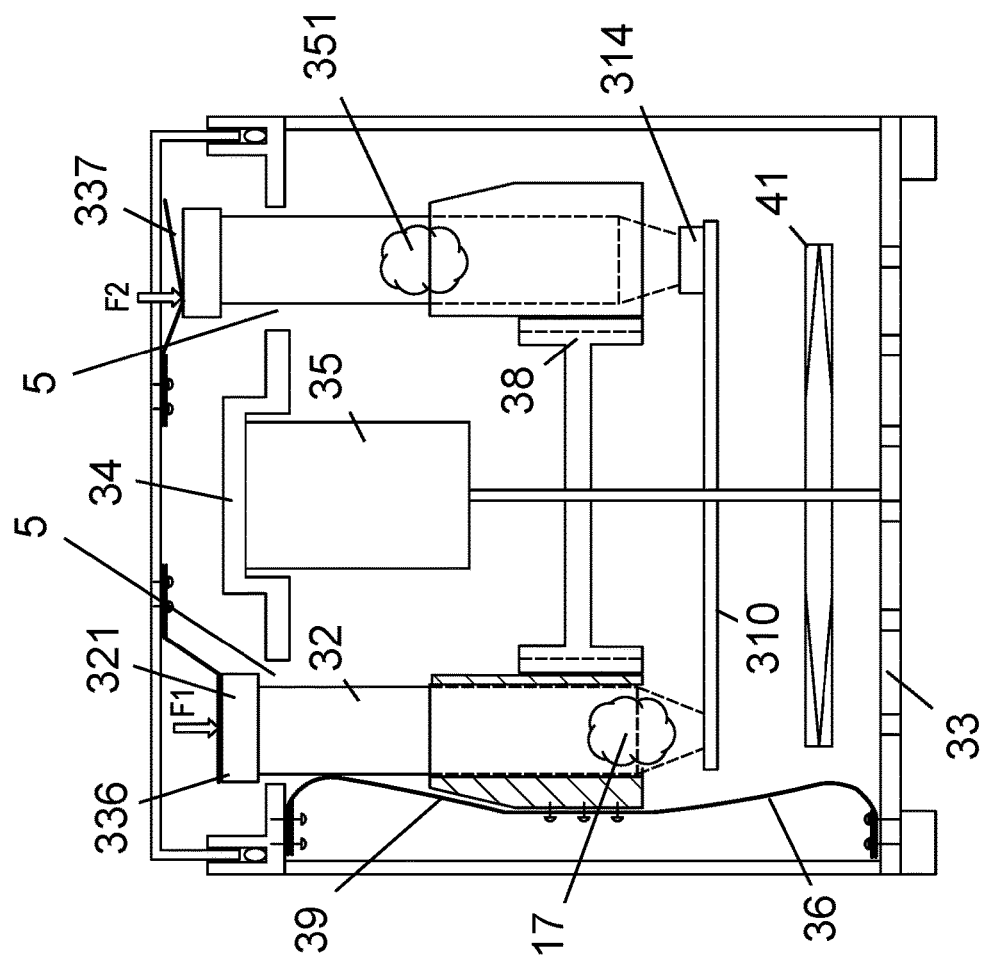
FIG. 5 shows a vertical cross-sectional view of an embodiment for both horizontal and vertical oscillation for disruption of large volume 50 ml test tubes.
Figure 6:
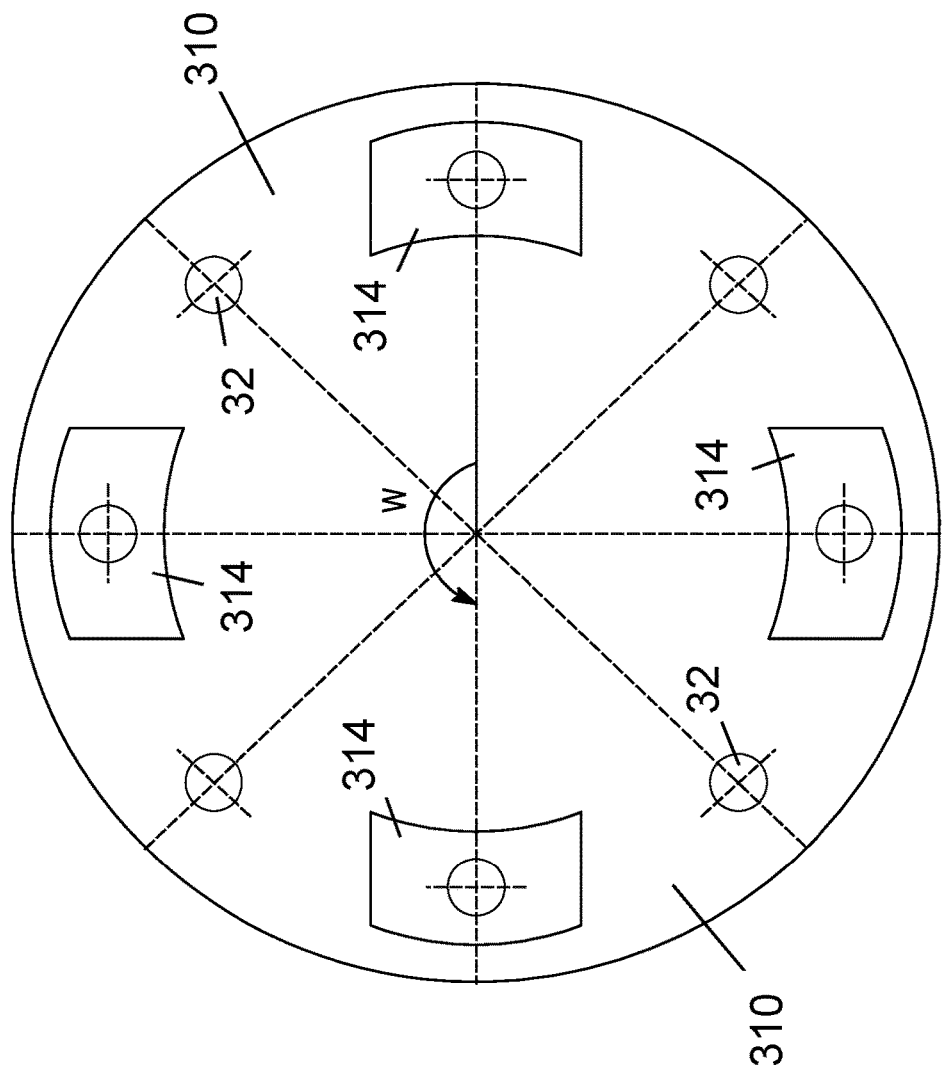
FIG. 6 shows a top view of an embodiment's rotating disk, supporting vertically-extended wedges.
Figure 7:
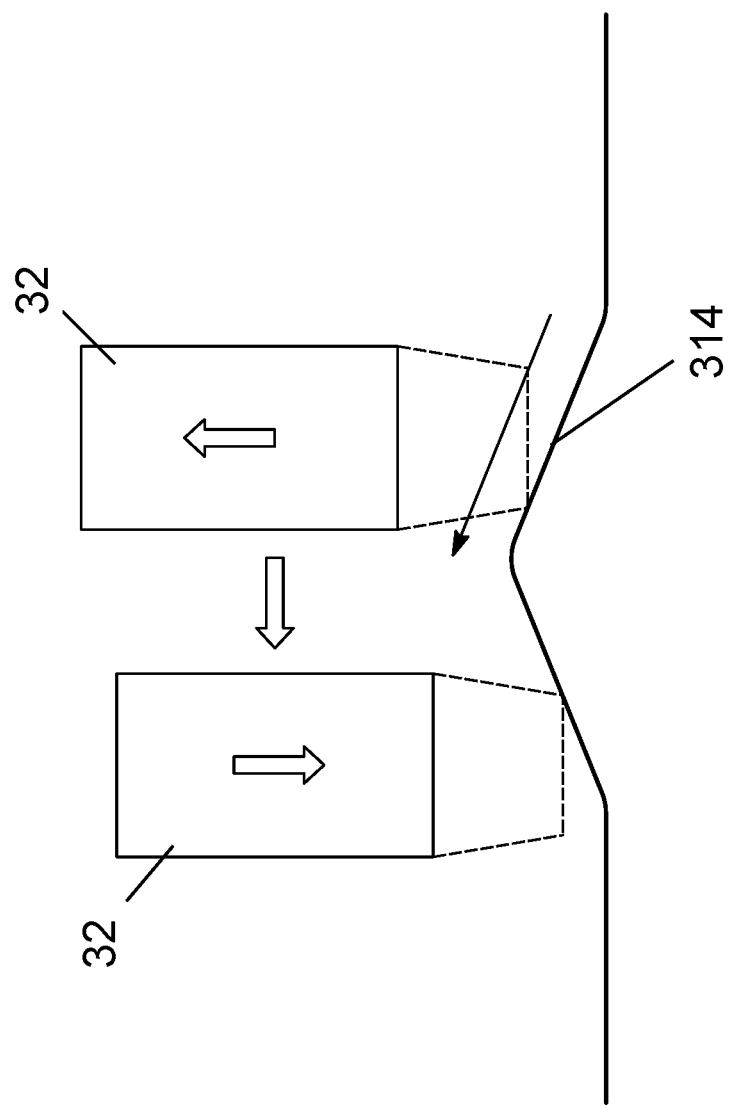
FIG. 7 shows a side view of one section of the embodiment in FIG. 5. The section illustrates the vertical pulsing motion of the test tubes due to contact with wedges when the rotating disk is rotated.
Figure 8:
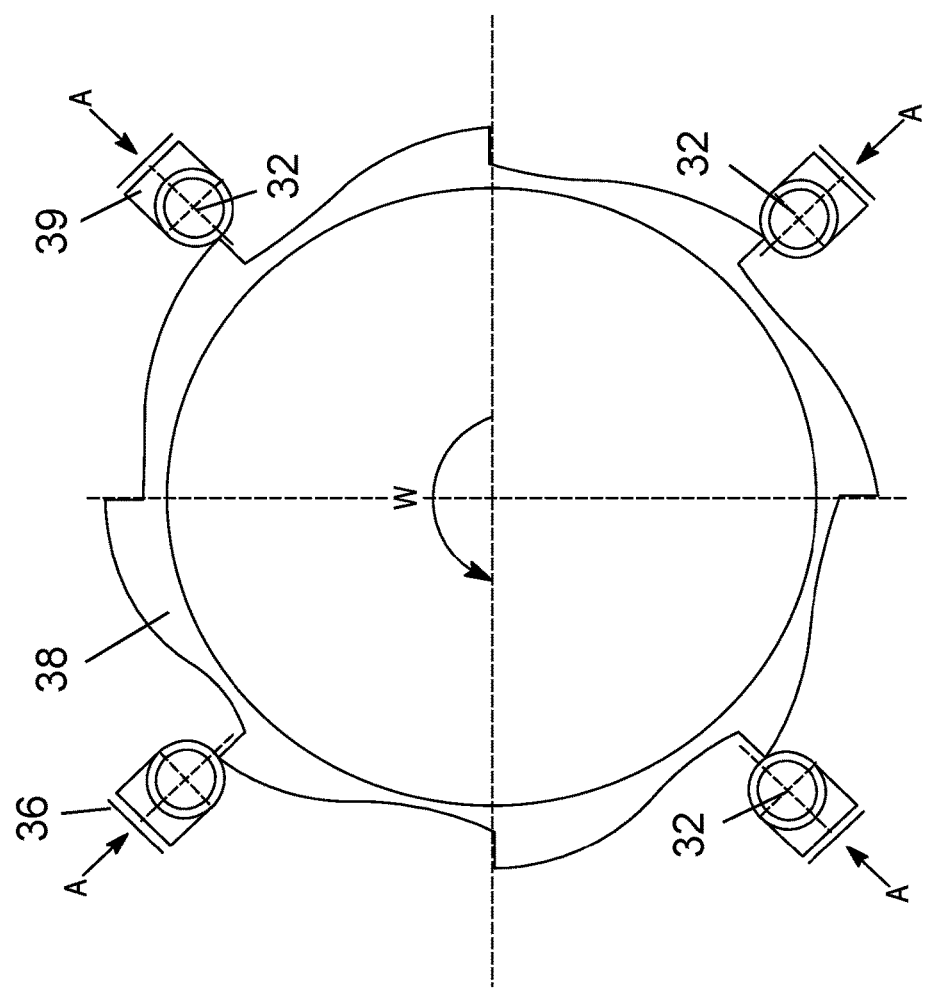
FIG. 8 shows a top view of an embodiment for horizontal oscillation in which the rotating ring is located centrally and test tubes are placed around the periphery.

A third embodiment shown in FIGS. 5-8 is capable of simultaneously processing big standard tubes of 50 ml, containing tissues of any hardness. The embodiment of FIG. 5 processes the tissues along two perpendicular axes. In FIG. 5, spring 36 extends from top plate 34 to the bottom plate 33 of housing 1. Spring 36 keep the tube supports 39 touching the revolving ring 38. Springs 36 are located adjacent to each tube support 39 and are hidden for clarity in FIG. 5. Tube supports 39 hold the tubes 32. The support's 39 height is approximately ⅓ of its tube's 32 length. The support is positioned toward the bottom of the tube 32. The bottom end of tube 32 is supported by rotating disk 310 which is rotated together with the rotating ring 38 by a motor 35. The support 39 is long enough to prevent wobbling of tube 32 inside the tube support 39 when the apparatus is rotating. Integrally attached to the rotating disk 310 are wedges 314, which are configured in circles about the axis of the rotating disk. The shape of wedges 314 vary much the same way that teeth 40 vary; the teeth may form a steady sine wave, may resemble jagged teeth, or may be virtually any shape in between.

Wedges 314, which are attached to the rotating disk 310, provide vertical lift to tubes. The rotating disk 310 rotates together with the ring 38. Wedges 314 extend upward from the rotating disk 310; the wedges are integrated onto the rotating disk. When the rotating disk 310 rotates, wedges 314 periodically travel under the tubes' bottoms and lift up the tubes, adding to the tube's oscillation.

To prevent tubes 32 from being ejected vertically out of their supports 39 when the tubes are pushed up by wedges 314, springs 336 press down on tube caps 321 as shown in FIG. 5. These springs 336 also enhance the energy of internal bead clashes because they produce an opposite downward force on the tubes 32 equal to the input force from the rotating disk. The beads inside the solution react with the contents of the tube as the tube is moved down by the spring or up rotating disk, causing more complete mixing and disruption of the substance 351. Springs 336 and 337 are attached to the top cover via traditional fastening means, and lay freely against the tube cap. F1 and F2 represent the varying forces applied by the springs 336 and 337. The force varies depending on whether a wedge is causing vertical displacement on the tube.

For larger tube processing, which can generate unwanted heat, one or more fans 41 powered by a motor 35 can blow air toward the tubes. A dry air box may also be placed beneath the housing knot shown). Both the one or more fans 41 and the dry air box may be a means for cooling the motor 35 and one or more vessels.

Figure 9:
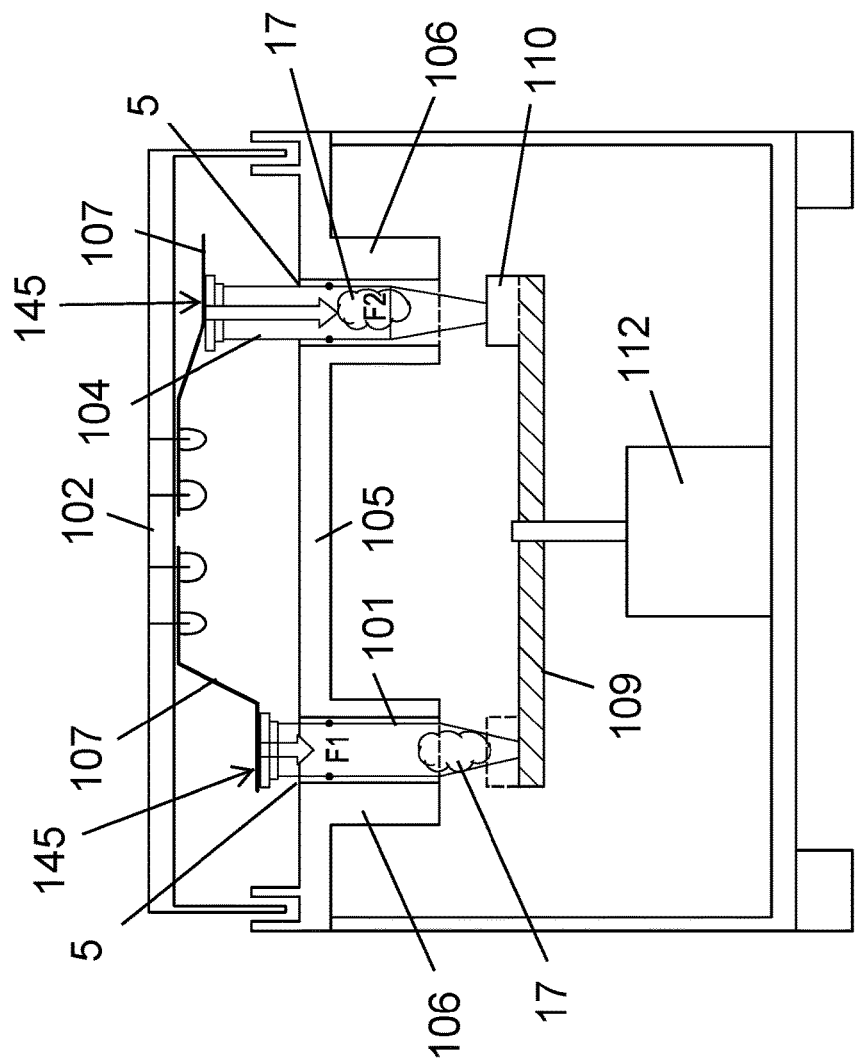
FIG. 9 shows a vertical cross-sectional view of an embodiment for vertical oscillation with a rotating disk and top-mounted springs.

A fourth embodiment is shown in FIGS. 9 and 10. FIG. 9 shows a vertical cross-section of a device for processing small tubes by only vertical pulsation of the tubes, similar to the method for vertical disruption described above. In this embodiment, no horizontal displacement occurs.

In FIG. 9, tubes 104 are shown moving vertically caused by the springs 107 providing forces F1 and F2 to react the vertical upward force created when the bottom end of the tubes 101 and 104 interface with a wedge 110 on the rotating disk 109. The springs 107 are attached to a cover 102 using bolts or other standard fastening means. The rotating disk 109 is powered by a motor 112. The tube is supported by a tube support 106 which is integral to the housing 105 which has openings into which the tubes are placed 106.

Figure 10A:
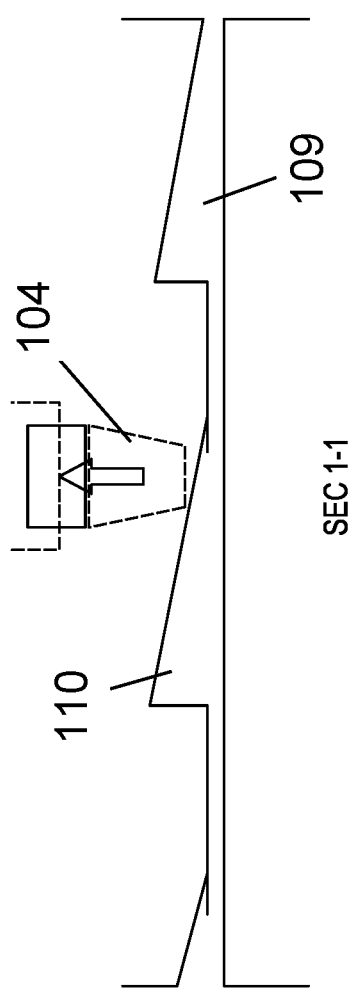
FIG. 10A shows a top view of the rotating disk in FIG. 9, with vertically-extending wedges.
Figure 10B:
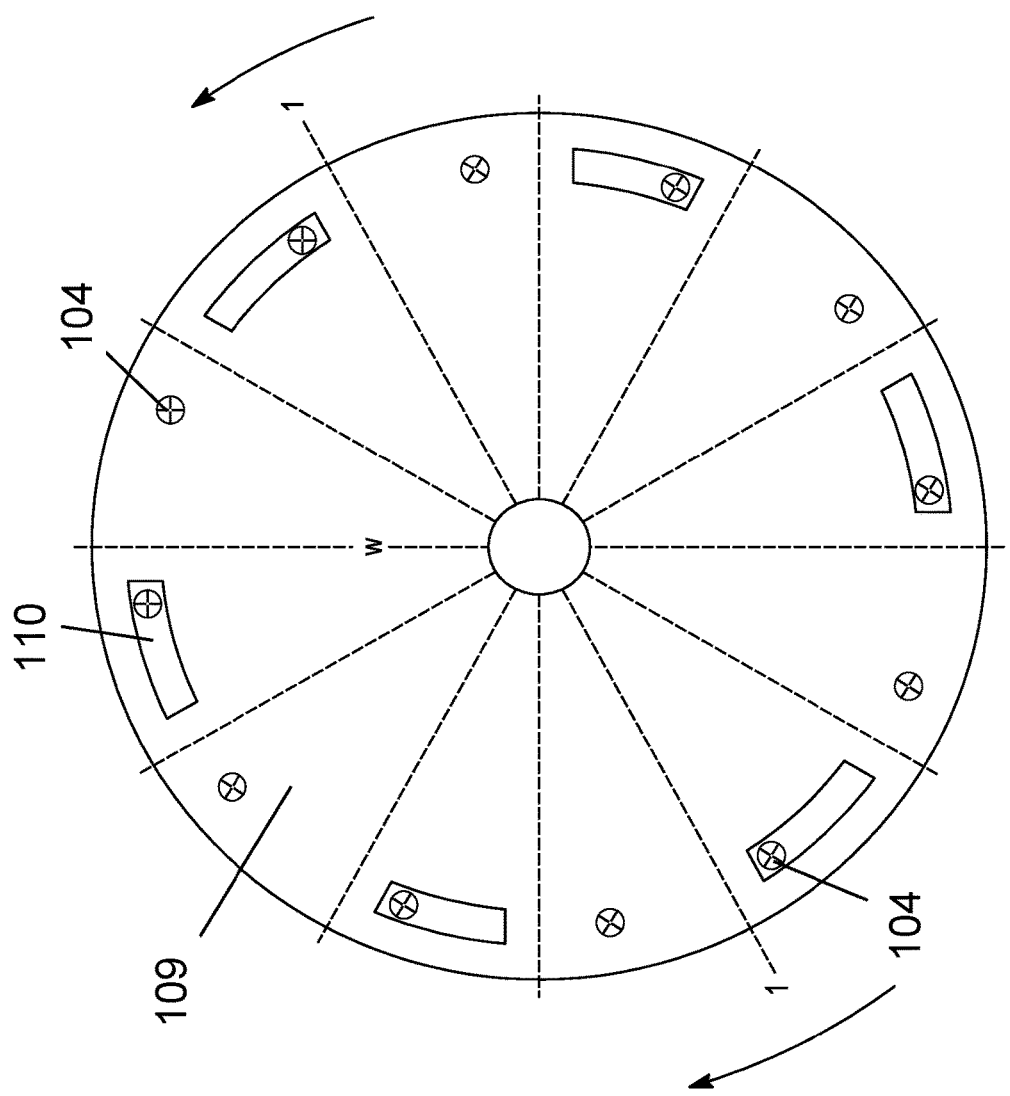
FIG. 10B shows a side view of the wedges on the rotating disk.

FIG. 10B shows a side view of the wedges 110 on the rotating disk 109. The profile and shape of the wedges can take many different forms from smooth curves to sharp steps as shown in FIG. 10B. Also shown in FIG. 10A is a top view of the rotating disk which shows the location of the various tube bottoms 104 and the placement of the wedges 110 on the rotating disk 109.

Figure 11:
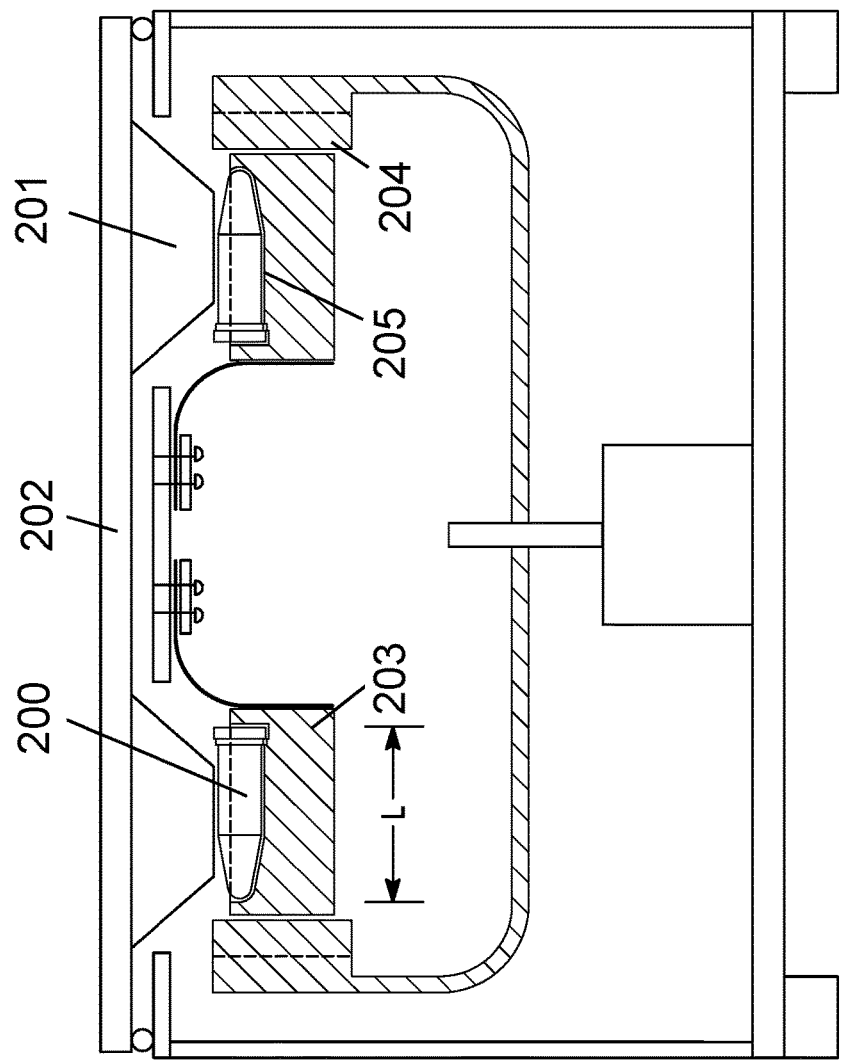
FIG. 11 shows a vertical cross-sectional view of an embodiment in which test tubes are positioned horizontally rather than vertically.
Figure 12:
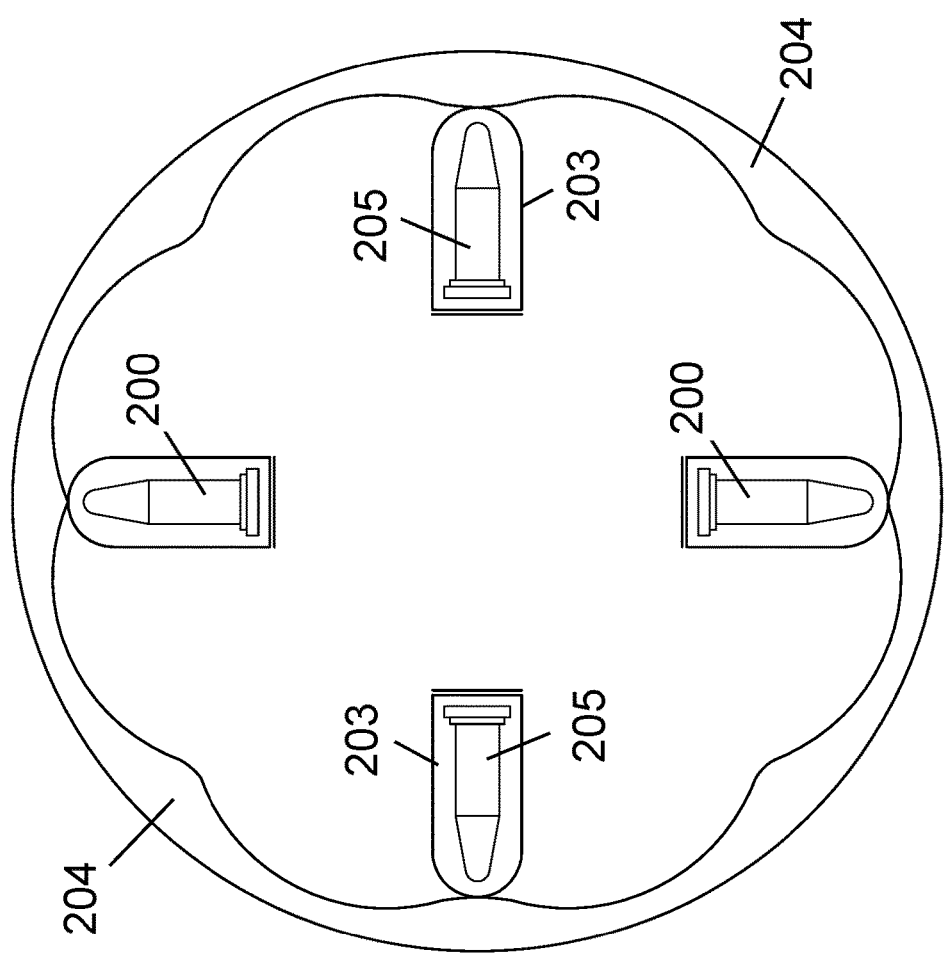
FIG. 12 shows a top section view of the arrangement of test tubes in FIG. 11.

A fifth embodiment is shown in FIGS. 11-12, in which test tubes supports 203, compartments 205, and test tubes 200 are arranged horizontally rather than vertically. Tube supports 203 and compartments 205 are built to accommodate tubes in a horizontal position. The rotating ring 204 is constructed substantially the same way as in the other embodiments. To prevent test tubes 200 from being ejected, top cover 202 has extensions 201 made of a material with a low friction factor with the material of the tubes.

The invention claimed is:

1. An apparatus for substantially horizontally oscillating one or more vessels containing a liquid, a solid, or a mixture thereof, comprising:
   a housing into which the one or more vessels are placed;
   one or more vessel supports having a compartment configured to hold each of the one or more vessels;
   a substantially circular rotating ring having a toothed inner circumference that rotates substantially horizontally about an axis, wherein the toothed inner circumference comes into contact with a radially outer portion of each of the one or more vessel supports, wherein the toothed inner circumference of the rotating ring causes substantially horizontal force on each of the one or more vessels when the toothed inner circumference comes into contact with the radially outer portion of each of the one or more vessel supports; and
   a spring, attached to the housing and in constant contact with each of the one or more vessel supports, wherein the spring provides continuous pressure on each of the one or more vessel supports against the toothed inner circumference of the rotating ring and counteracting the force exerted by the toothed inner circumference of the rotating ring, thus creating substantially horizontal displacements of each of the one or more vessel supports and each of the one or more vessels during the ring's rotation.

2. The apparatus according to claim 1, further comprising a removable closure maintaining the position of each of the one or more vessels in each of the one or more vessel supports when the rotating ring is rotating.

3. The apparatus according to claim 2, further comprising one or more springs attached to the closure, causing the closure to continuously contact a cap, located on top of each of the one or more vessels, forcing each of the one or more vessels downward.

4. The apparatus according to claim 1, wherein a gap exists on either side of each of the one or more vessels and each of the one or more vessel supports, allowing additional striking movement of each of the one or more vessels inside each of the one or more vessel supports, resulting in simultaneous mixing of striking and oscillation.

5. The apparatus according to claim 1, further comprising a motor to rotate the rotating ring about said axis.

6. The apparatus according to claim 5, further comprising a means for cooling the motor and each of the one or more vessels.

7. The apparatus according to claim 1, wherein each of the one or more vessel supports is configured to contain each of the one or more vessels.

8. The apparatus according to claim 1, wherein the rotating ring has one or more protruding teeth directed radially inward toward each of the one or more vessel supports along the inner circumference of the rotating ring.

9. An apparatus for substantially vertically oscillating one or more vessels containing a liquid, a solid, or a mixture thereof, comprising:
   the one or more vessels each contained in a vessel support;
   a substantially horizontally rotating disk;
   the rotating disk having one or more wedges on one or more surfaces, wherein the one or more wedges of the rotating disk comes into contact with a bottom of the one or more vessels, wherein the one or more wedges of the rotating disk causes substantially vertical force on the one or more vessels when the one or more wedges comes into contact with the bottom of the one or more vessels; and
   a spring, attached to the housing and in constant contact with the top of the one or more vessels, wherein the spring provides downward force on the one or more vessels counteracting the force exerted by the one or more wedges of the rotating disk, thus causing one or more oscillations each time the one or more vessels comes into contact with the one or more wedges of the rotating disk.

10. The apparatus according to claim 9, further comprising a motor to rotate the rotating-disk.

11. The apparatus according to claim 9, wherein each of the one or more wedges directed toward each of the one or more vessels are disposed on the horizontally rotating disk.

12. The apparatus according to claim 9, wherein each of the one or more wedges are greater than 0 degrees and less than 45 degrees in angle as measured from the rotating disk, providing gentle oscillation of each of the vessel supports and vessels.

13. The apparatus according to claim 9, wherein each of the one or more wedges are greater than 45 and less than 90 degrees in angle as measured from the rotating disk, and provide forceful oscillation of each of the vessel supports and vessels.

14. The apparatus according to claim 9, wherein two of the one or more wedges are unequal in shape and size, thereby varying the timing and size of vessel oscillations.

15. The apparatus according to claim 9, further comprising a removable closure maintaining the position of each of the one or more vessels in each of the one or more vessel supports when the rotating disk is rotating.

16. The apparatus according to claim 9, wherein a gap exists on either side of each of the one or more vessels and each of the one or more vessel supports, allowing additional striking movement of each of the one or more vessels inside each of the one or more vessel supports, resulting in simultaneous mixing of striking and oscillation.

17. The apparatus according to claim 9, further comprising a motor to rotate the rotating disk.

18. The apparatus according to claim 17, further comprising a means for cooling the motor and each of the one or more vessels.

19. The apparatus according to claim 9, wherein the rotating disk has one or more of said wedges directed toward each of the one or more vessel supports along each of the one or more surfaces of the rotating disk.

* * * * *